United States Patent [19]

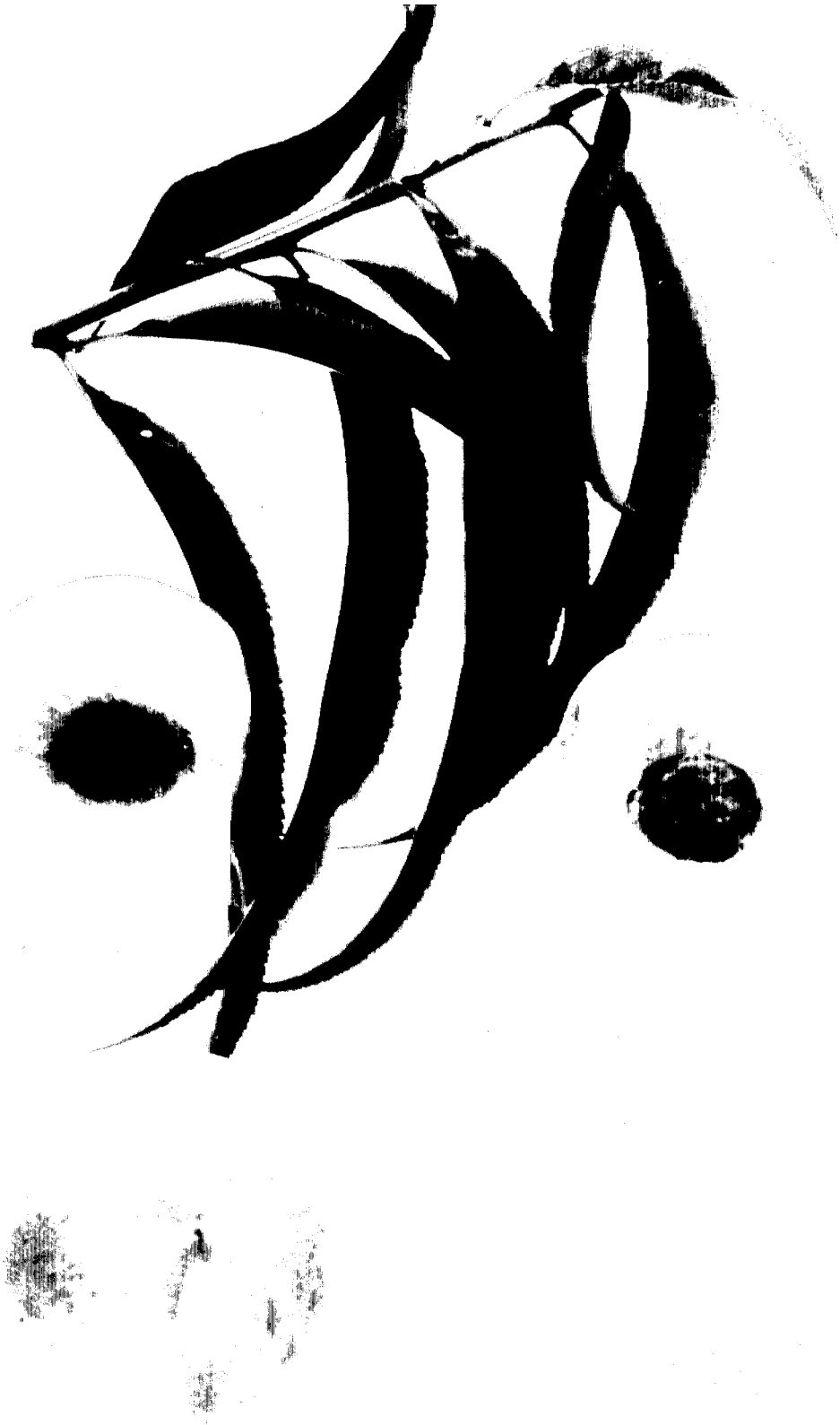

Zaiger et al.

[11] Patent Number: Plant 5,745

[45] Date of Patent: May 13, 1986

[54] PEACH TREE ("TOP CREST")

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 672,048

[22] Filed: Nov. 16, 1984

[51] Int. Cl.[4] ..... A01H 5/03

[52] U.S. Cl. ..... Plt./43

[58] Field of Search ..... Plt./43

*Primary Examiner*—Robert E. Bagwill

[57] ABSTRACT

A new and distinct variety of peach tree which has the following unique combination of desirable features:

1. Early maturity of fruit (ripening 2 to 3 days before Royal April Peach (U.S. Plant Pat. No. 3,411).
2. Heavy production.
3. Extreme firmness of the flesh with excellent shipping characteristics.
4. Good handling and packing characteristics due to round shape.
5. Good eating and storage quality.

1 Drawing Figure

ORIGIN OF THE VARIETY

Our new variety of peach tree was originated by us in the experimental orchard located at Modesto, Calif. It was selected from a large group of first generation seedlings originating from a cross between Fayette Peach (Non-patented) and a peach seedling of unknown parentage. We maintained this new selection under close observation, during which time we recognized its distinctive desirable characteristics described above and selected the variety for asexual reproduction and commercialization.

ASEXUAL REPRODUCTION OF THE VARIETY

The present variety of peach tree was asexually reproduced by budding as performed by us in the experimental orchard at Modesto, Calif. and shows that said characteristics come true to form and are established and transmitted through succeeding propagations.

SUMMARY OF THE VARIETY

The present variety of peach tree is of large size, vigorous, upright growth and a regular and productive bearer of medium to large size, very firm, yellow flesh, clingstone fruit with good eating quality and the ability to store and ship to long distance markets. The fruit is further characterized in comparison to Royal April Peach (U.S. Plant Pat. No. 3,411) by being more round in shape, having firmer flesh, greater storage and shipping quality and ripening 2 to 3 days earlier.

BRIEF DESCRIPTION OF THE PHOTOGRAPHS

The accompanying photographs show reproductions of typical specimens of the fruit and foliage of our new variety, with illustrations of the upper and lower surface of the foliage, and an exterior and sectional view of the fruit with the stone in place. The photographs were taken shortly after being picked at maturity (firm ripe) and the colors are as nearly true as is reasonably possible in a color representation of this type.

DESCRIPTION OF THE VARIETY

The botanical details of our new and distinct variety of peach tree, as based on observations of specimens grown at Modesto, Calif., with color terminology (except those in common color terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Production.*—Productive.
- *Bearer.*—Regular.

Trunk:
- *Size.*—Stocky.
- *Texture.*—Medium shaggy.
- *Color.*—Brownish gray.

Branches:
- *Size.*—Medium stocky.
- *Texture.*—Smooth to medium rough.
- *Lenticels.*—Numerous. Medium size.
- *Color.*—Brown to grayish brown.

Leaves:
- *Size.*—Large. Average length — 7". Average width — $1\frac{5}{8}$".
- *Form.*—Lanceolate, pointed.
- *Texture.*—Smooth.
- *Thickness.*—Medium.
- *Margin.*—Crenate.
- *Petiole.*—Average length — 1". Average width — 3/32".
- *Glands.*—Average number 4, range 2 to 6. Positioned on lower part of leaf blade and upper part of petiole. Reniform.
- *Color.*—Upper surface — Deep green (27-F-5) to (28-F-6). Lower surface — grayish green (28-E-6) to (28-E-7).

Flower buds:
- *Size.*—Medium to large.
- *Form.*—Plump.
- *Pubescence.*—Pubescent.

Flowers:
- *Size.*—Large, showy.
- *Blooming period.*—Feb. 26, 1982 to Mar. 7, 1982. Varies slightly with climatic conditions.
- *Pollen.*—Present.
- *Color.*—Pink.

Fruit:
- *Maturity when described.*—Firm ripe.

*Date of first picking.*—May 8, 1982.
*Date of last picking.*—May 16, 1982.
*Size.*—Medium to large. Average diameter axially — 2 5/16" to 2⅞". Average diameter transversely to suture plane — 2 5/16" to 2⅞".
*Form.*—Globose — Nearly symmetrical.
*Suture.*—Shallow — extends from apex to base.
*Ventral surface.*—Nearly rounded.
*Apex.*—Rounded to slightly retuse.
*Base.*—Retuse.
*Cavity.*—Rounded to slightly elongated. Average depth — ½". Average breadth — 11/16".

Skin:
*Thickness.*—Medium.
*Texture.*—Medium.
*Tendency to crack.*—None.
*Down.*—Moderate. Short.
*Color.*—Bright yellow ground color — (4-A-8) to (5-A-8). Red blush (8-A-7) to (8-B-8).

Flesh:
*Texture.*—Very firm.
*Fibers.*—Few — tender.
*Juice.*—Moderate.
*Amygdalin.*—Wanting.
*Ripens.*—Evenly.
*Flavor.*—Mild.
*Aroma.*—Very little.
*Eating quality.*—Good.
*Color.*—Dark yellow (4-A-7) to (4-A-8) to cadmium orange (5-A-6) to (5-A-7). Stone cavity — red (9-A-6) to (9-A-8) bleeding into sections of flesh around cavity.

Stone:

*Type.*—Clingstone.
*Size.*—Medium. Average length — 1 3/16". Average breadth — ⅞". Average thickness — ⅝".
*Form.*—Ovid.
*Base.*—Mostly straight.
*Apex.*—Acuminate.
*Sides.*—Mostly equal.
*Surface.*—Furrowed toward apex. Pitted toward base.
*Ridges.*—Rounded.
*Tendency to split.*—Slight.
*Color.*—Light brown (8-C-5) to (8-D-6).

Use: Dessert.
*Market.*—Local and long distance.
Shipping quality: Very good.
Keeping quality: Very good.

The new peach tree and its fruit herein described, may vary in slight detail due to climatic, soil conditions and cultural practices under which the variety may be grown, the present description being of the variety as grown by us in the experimental orchard under ecological conditions prevailing at Modesto, Calif.

The following is claimed:

1. A new and distinct variety of peach tree, substantially as illustrated and described, characterized by its large size, vigorous and upright growth and being a regular and productive bearer of medium to large, very firm, yellow flesh, clingstone fruit; the fruit is further characterized in comparison to Royal April Peach (U.S. Plant Pat. No. 3,411), by maturing 2 to 3 days earlier, being more round in shape, having firmer flesh and greater storage and shipping characteristic.

* * * * *